United States Patent [19]

Nebolon

[11] Patent Number: 5,383,845
[45] Date of Patent: Jan. 24, 1995

[54] HINGED ORTHOPEDIC BRACE HAVING COMPLIANT SUPPORT COMPONENTS

[75] Inventor: Joseph F. Nebolon, Del Mar, Calif.

[73] Assignee: Smith & Nephew Donjoy Inc., Carlsbad, Calif.

[21] Appl. No.: 17,032

[22] Filed: Feb. 12, 1993

[51] Int. Cl.⁶ .............................................. A61F 5/00
[52] U.S. Cl. ........................................ 602/26; 602/16
[58] Field of Search ................... 602/5, 16, 20, 21, 23, 602/26

[56] References Cited

U.S. PATENT DOCUMENTS

| | | | |
|---|---|---|---|
| 3,387,305 | 6/1968 | Shafer | 602/26 X |
| 3,581,741 | 6/1971 | Rosman | 602/26X |
| 3,669,105 | 6/1972 | Castiglia | |
| 4,191,373 | 3/1980 | Lancellotti | 602/16 X |
| 4,381,768 | 5/1983 | Erichsen et al. | 602/26 X |
| 4,506,661 | 3/1985 | Foster | |
| 4,633,867 | 1/1986 | Kausek et al. | |
| 4,686,969 | 8/1987 | Scott | 602/16 X |
| 4,697,583 | 10/1987 | Mason et al. | |
| 4,791,916 | 12/1988 | Paez | |
| 4,805,606 | 2/1989 | McDavid, III | 602/26 |
| 4,854,308 | 8/1989 | Drillio | 602/16 |
| 4,955,369 | 9/1990 | Bledsoe et al. | |
| 5,016,621 | 5/1991 | Bender | |
| 5,063,916 | 11/1991 | France et al. | |

FOREIGN PATENT DOCUMENTS

| | | | |
|---|---|---|---|
| 521722 | 4/1982 | Australia | A61F 5/01 |
| 1201951 | 3/1986 | Canada | 602/26 |
| 2627381 | 8/1989 | France | A61F 5/10 |
| 1024204 | 2/1958 | Germany | . |
| 3040595 | 1/1982 | Germany | 602/26 |
| 3520939 | 12/1986 | Germany | 602/26 |
| 4013693 | 8/1991 | Germany | 602/26 |
| 2136294 | 9/1984 | United Kingdom | 602/26 |

Primary Examiner—Richard J. Apley
Assistant Examiner—Linda C. M. Dvorak
Attorney, Agent, or Firm—Rodney F. Brown

[57] ABSTRACT

An orthopedic brace for supporting a joint has a plurality of compliant support components, including a hinged shell of stiffened elastic material and at least one supple support strap engaging the brace at two points on opposite sides of the hinge to stabilize the weakened joint throughout its range of motion, The shell has a pair of cuffs adapted to engage the body adjacent to the joint and connected to one another across a rotatable hinge by arms integrally extending from the cuffs, The support strap is adjustable in length enabling the user to modify the support strap tension, and consequently the degree of support the brace provides to the joint.

24 Claims, 5 Drawing Sheets

HINGED ORTHOPEDIC BRACE HAVING COMPLIANT SUPPORT COMPONENTS

TECHNICAL FIELD

The present invention relates generally to orthopedic braces, and more particularly to a hinged orthopedic brace that is substantially free of any rigid support components, thus, having only compliant support components.

BACKGROUND OF THE INVENTION

Orthopedic braces are commonly employed on the body of a user to stabilize a skeletal joint that has been weakened by injury or other infirmity. Such braces are made up of a number of rigid support components that are dynamically linked together by one or more hinges to support the joint during user activity. The brace is positioned on the body such that the hinges traverse the joint being stabilized, while the rigid components are secured to the body at a plurality of contact points above and below the joint. Typical hinged orthopedic brace constructions are disclosed in U.S. Pat. Nos. 4,633,867; 4,697,583; and 5,063,916.

The utility of conventional hinged orthopedic braces is, however, diminished by a number of drawbacks. The rigid components of conventional braces are bulky and noncompliant, often rendering them uncomfortable for the everyday user and difficult to initially size and fit. Conventional braces pose additional problems for athletic users. Specifically, certain athletic competitions, such as soccer and rugby, have rules barring the use of braces with rigid protruding components because the components create a risk of injury to other players from contact therewith. Conventional braces can also be disadvantageous to the athletic user because the braces have an irregular surface which reduces the desired ability of the user to control balls or other objects impacting the surface and rebounding therefrom during athletic competitions.

Accordingly, it is an object of the present invention to provide an orthopedic brace that overcomes the above-described drawbacks. In particular, it is an object of the present invention to provide a hinged orthopedic brace that provides the user with a high degree of comfort while wearing the brace. It is also an object of the present invention to provide a hinged orthopedic brace having compact components for ease of sizing and fitting. It is further an object of the present invention to provide a hinged orthopedic brace having only compliant support components, i.e., a hinged orthopedic brace that is substantially free of any rigid support components, yet which provides for control and stability of the desired joint. It is another object of the present invention to provide a hinged orthopedic brace that may be used in athletic competitions having rules barring braces with rigid support components. It is yet another object of the present invention to provide a hinged orthopedic brace having a relatively even, flush surface that reduces the risk of injuries to others coming in contact therewith and that permits greater control of balls or other objects rebounding therefrom during athletic competitions.

SUMMARY OF THE INVENTION

The present invention is an orthopedic brace for supporting a joint throughout its range of motion when the brace is mounted about the joint on a limb of a user. The support components of the brace are a hinged shell formed from a compliant, yet stiffened, material that conforms to the contours of the limb and a pair of supple support straps engaging the shell at specific points thereon. The shell is configured to maintain a predetermined dynamic relationship between the support straps and the joint as the joint moves through its range of motion, thereby enabling the support straps to stabilize an injured or otherwise weakened joint. All of the support components of the brace are fully compliant and, thus, the brace is substantially free of any rigid support components.

The brace can be adapted to support any one of a number of joints on the limbs of the body, including the wrist, elbow and knee. In each case, the stiffened elastic shell comprises a proximal cuff and a distal cuff adapted to proximally and distally engage the limb about the joint, respectively, with the cuffs preferably positionable on opposite sides of the limb.

The shell further comprises a lateral proximal arm and a medial proximal arm, each connected to the proximal cuff and extending therefrom in a distal direction generally longitudinal to the proximal portion of the limb. Additionally, the shell comprises a lateral distal arm and a medial distal arm, each connected to the distal cuff and extending therefrom in a proximal direction generally longitudinal to the distal portion of the limb.

The brace is provided with a hinge at the lateral and medial junctions of the proximal and distal arms adjacent to the joint which enables rotation of the proximal cuff about the joint relative to the distal cuff. In particular, the hinge comprises a lateral pin pivotally connecting the lateral proximal arm to the lateral distal arm, and a medial pin pivotally connecting the medial proximal arm to the medial distal arm.

Both support straps are anchored to the brace at a proximal engagement point and at a distal engagement point. In addition to being proximally or distally positioned, the engagement points are further either anteriorly or posteriorly positioned on opposite sides of the brace from one another. One support strap is a lateral support strap extending from the proximal engagement point around the lateral side of the joint to the distal engagement point, and the remaining support strap is a medial support strap extending from the proximal engagement point around the medial side of the joint to the distal engagement point.

The proximal and distal engagement points are preferably located at substantially central positions on the proximal and distal cuffs, respectively. The support straps are fully adjustable in length enabling the user to modify, as desired, the support strap tension, and consequently the degree of support the brace provides to the joint.

A plurality of proximal and distal shell retention straps are provided in engagement with the shell which enable closure of the brace around the limb. The shell retention straps retain the shell in a desired stable position on the limb about the joint. Guide straps are provided in attachment to the support straps and extend therefrom for connection to the shell. The guide straps function in conjunction with the shell to guide the support straps as the joint moves through its range of motion.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
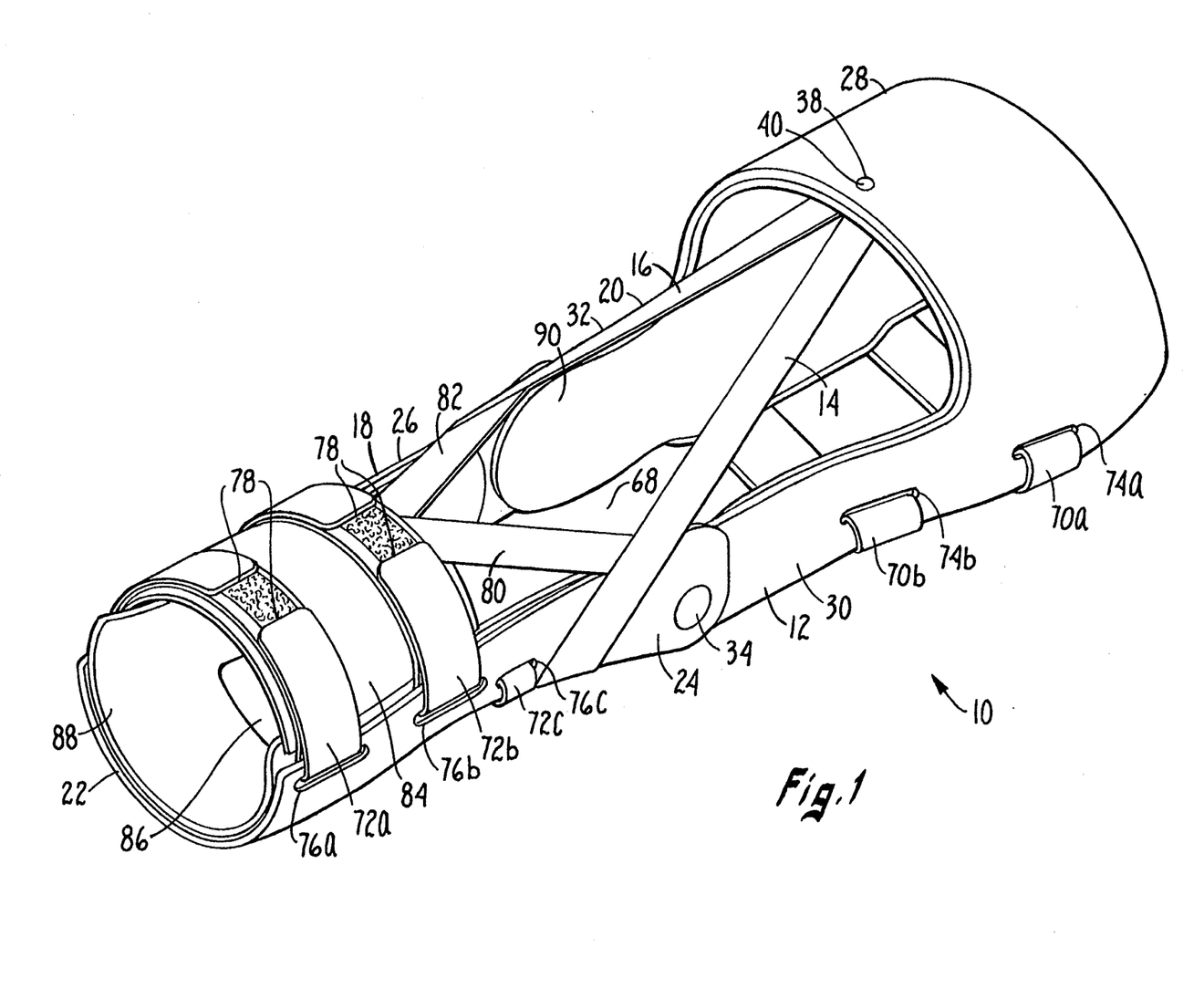
FIG. 1 is a frontal perspective view of an embodiment of the orthopedic brace of the present invention adaptable to the knee joint or other body joints.

Referring initially to FIG. 1, an orthopedic brace of the present invention is shown and generally designated 10. Although the brace as shown is adapted for mounting on the left leg of a user about the knee joint in support thereof, it is understood that the brace of the present invention has general utility for mounting on the limbs of the body about any joint that pivots in a single plane of motion, including the knee, elbow, and wrist. As is readily apparent to the skilled artisan, the brace configuration shown in FIG. 1 requires only slight modification for adaptation to any such joint.

Brace 10 comprises a plurality of compliant support components including a shell 12, a lateral support strap 14, and a medial support strap 16. The compliant shell 12 has a distal portion 18 conformable to the lower leg and a proximal portion conformable to the upper leg. The distal portion 18 is preferably formed from a single continuous shaped piece of a stiffened sheet material that is resiliently bendable, i.e., elastic, in the vertical plane to readily conform to the body contours of the user, but is substantially unstretchable, i.e., inelastic, in the horizontal plane to provide a secure anchor for support straps 14, 16, as will be described hereafter. Materials which satisfy these criteria include certain plastics, fiberglass, and like compositions as are readily known to one skilled in the art.

The integral elements of distal portion 18 include a distal (or calf) cuff 22, having a lateral distal arm 24 and medial distal arm 26 extending proximally therefrom. The proximal portion 20 is likewise preferably formed from a single continuous shaped piece of a stiffened sheet material having the same characteristics as distal portion 18. The integral elements of proximal portion 20 include a proximal (or thigh) cuff 28, having a lateral proximal arm 30 and medial proximal arm 32 extending distally therefrom.

Lateral distal arm 24 is pivotally connected to lateral proximal arm 30 and medial distal arm 26 is pivotally connected to medial proximal arm 32 across a hinge means comprising a lateral pin 34 and a medial pin 36 (shown in FIG. 2), respectively. Pins 34, 36 are preferably rivets rotatably fastening arm 24 to arm 30 and arm 26 to arm 32, respectively.

Figure 2:
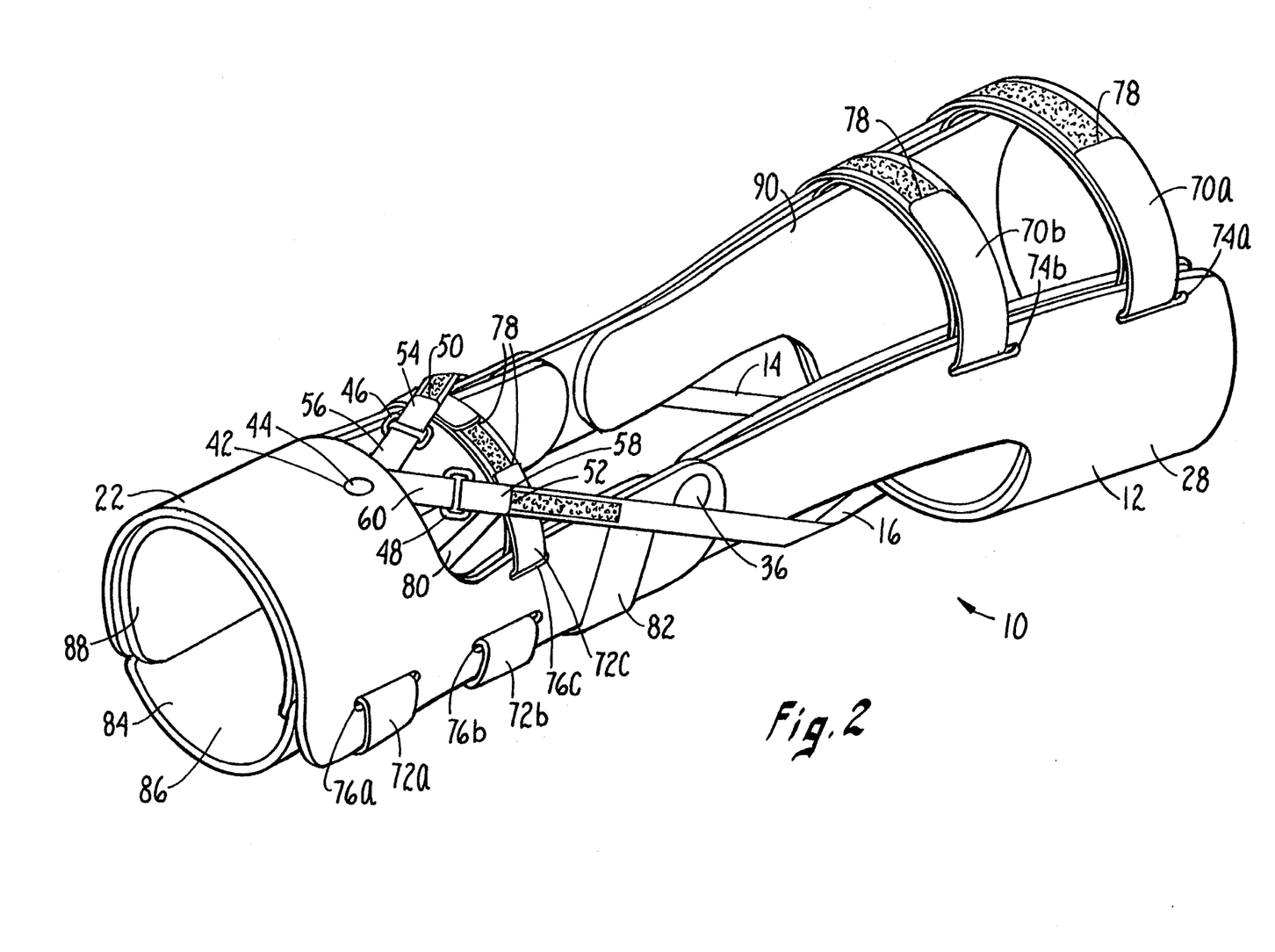
FIG. 2 is a rear perspective view of the orthopedic brace of FIG. 1.

Support straps 14, 16 are formed from a wear-resistant supple material such as pliant leather, or preferably natural or synthetic cloth, including nylon and the like, which is compliant, but substantially unstretchable. Both support straps 14, 16 are connected to shell 12 by fixably engaging shell 12 at a proximal engagement point 38 substantially centrally located on the proximal cuff 28. Fixable engagement of the support straps 14, 16 and proximal cuff 28 is secured by a rivet 40 extending therethrough. Referring to FIG. 2 in conjunction with FIG. 1, support straps 14, 16 are further shown connected to shell 12 by fixably engaging shell 12 at a distal engagement point 42 substantially centrally located on the distal cuff 22. Fixable engagement of the support straps 14, 16 and distal cuff 22 is secured by a rivet 44 extending therethrough.

Support straps 14, 16 can be formed from two separate lengths of strap having ends that are connected at engagement points 38 and 42 by rivets 40 and 44, respectively. Alternatively, support straps 14, 16 can be formed from a single length of strap that is continuous at engagement point 38 or 42, but having two free ends that are connected at the opposite engagement point 38 or 42 by rivet 40 or 44, respectively.

In either case, adjustment of the length of support straps 14, 16 is provided, as shown in FIG. 2, by including adjustment loops 46, 48 and hook and loop fasteners 50, 52, commonly termed VELCRO fasteners, along the length of straps 14, 16. Strap 14 has an end 54 adjustably attached to loop 46 by threading end 54 through loop 46 and doubling end 54 back onto itself for fastening thereto by fastener 50. Strap 14 further has a fixed length portion 56 fixably attached to loop 46 which extends to rivet 44 at distal engagement point 42. Likewise, strap 16 has an end 58 adjustably attached to loop 48 and a fixed length portion 60 fixably attached to loop 48 and extending to rivet 44 in substantially the same manner as strap 14.

Figure 3:
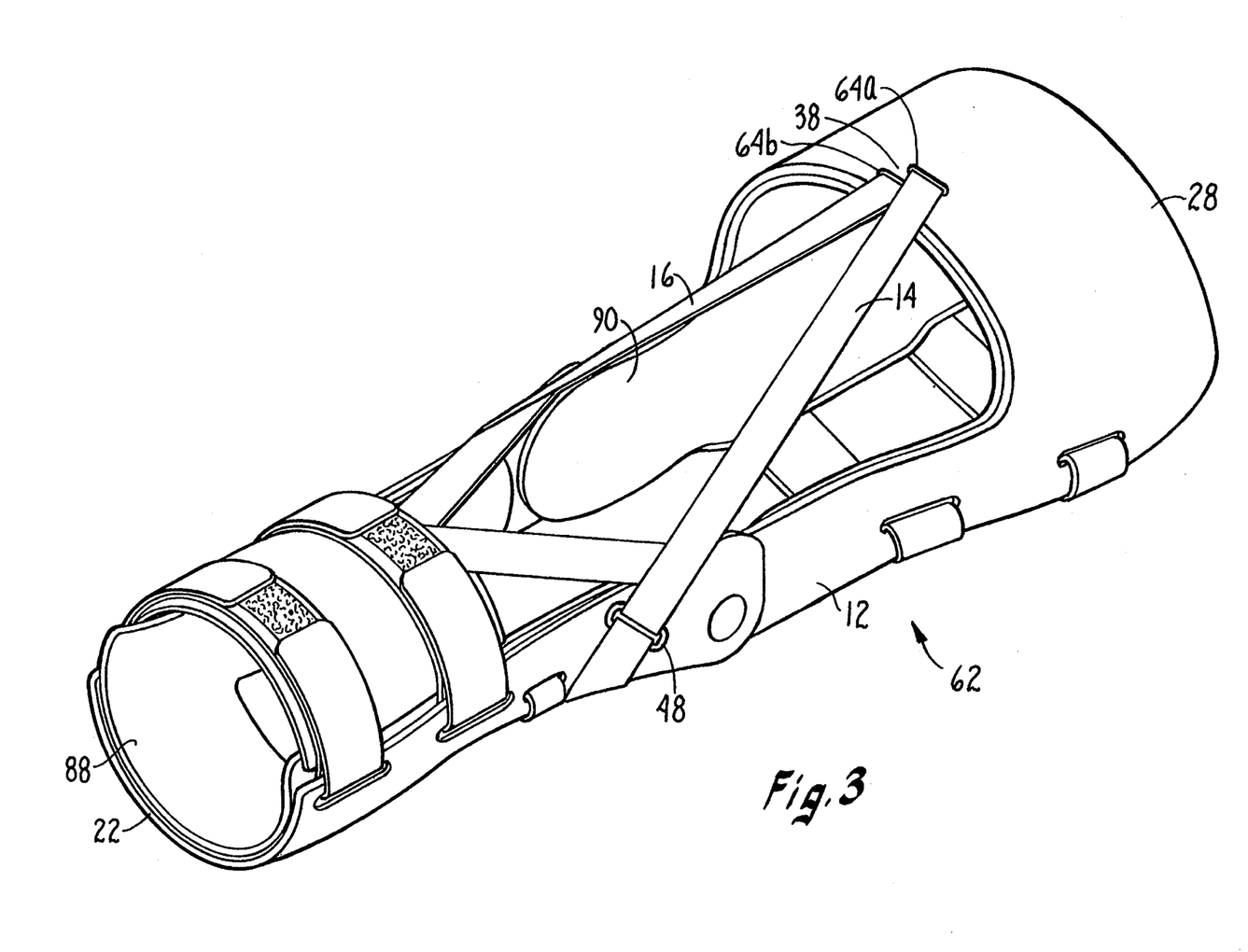
FIG. 3 is a frontal perspective view of an alternate embodiment of the orthopedic brace of the present invention adaptable to the knee joint or other body joints.

An alternate embodiment of the support strap and shell engagement means is shown on a brace generally designated 62 in FIG. 3. The support straps 14, 16 of brace 62 are formed from a single length of strap that is continuous at the proximal engagement point 38 centrally located on the proximal cuff 28. The continuous length of strap is partitioned into the two support straps 14, 16 at the engagement point 38 by looping the strap through a pair of engagement slots 64a, 64b formed in cuff 28 which provide slidable engagement between the cuff 28 and the support straps 14, 16. Although not shown in FIG. 3, the two free ends of the length of strap are fixably connected at the distal engagement point by a rivet through the strap ends and distal cuff 22 in the same manner as shown in FIG. 2 and described above.

It is understood that the proximal position of slots 64a, 64b can be reversed with the distal position of the rivet in brace 62 such that slots 64a, 64b are formed in the distal cuff 22 and the rivet is placed in the proximal cuff 28 to achieve essentially the same objective. In substantially all other respects, brace 62 is identical to brace 10. Accordingly, it is noted that loops 48 are provided in the same manner as brace 10 (only one loop 48 is shown here on lateral distal arm 24) to enable adjustment of support straps 14, 16.

Referring to both the embodiment of FIGS. 1 and 2 and the embodiment of FIG. 3, it is shown that the lateral support strap 14, extends laterally from the proximal engagement point 38 across an opening 68 in shell 12 framed by arms 24, 26, 30, 32 to the distal engagement point 42. Conversely, the medial support strap 16 extends medially from the proximal engagement point 38 across opening 68 to the distal engagement point 42.

Braces 10 and 62 are further provided with a plurality of proximal shell retention straps 70a, 70b and a plurality of distal shell retention straps 72a, 72b, 72c which are in engagement with the shell 12 by threading them through proximal retention slots 74a, 74b and distal retention slots 76a, 76b, 76c, respectively. In a preferred configuration, distal shell retention strap 72c is positioned on the opposite side of shell 12 from distal shell retention straps 72a, 72b. However, it is understood that other retention strap configurations are possible within the scope of the present invention.

Retention straps 70a, 70b, 72a, 72b, 72c enable closure of brace 10 or 62 around the limb on which the brace is mounted. Each retention strap 70a, 70b, 72a, 72b, 72c is integrally provided with a hook and loop fastener 78 at the ends thereof to enable release of the retention strap or adjustment to the length of the retention strap for close conformance of the shell 12 to the limb on which the brace is mounted.

A lateral guide strap 80 having two ends is fixably attached at its one end by means such as stitching to lateral support strap 14. A medial guide strap 82 having two ends is similarly attached at its one end to medial support strap 16. Guide straps 80 and 82 extend laterally and medially, respectively, to a retention member that is shown herein to be a distal shell retention strap 72b. The opposite ends of both guide straps 80 and 82 are fixably attached to the distal shell retention strap 72b by means such as stitching. Guide straps 80, 82 and retention straps 70a, 70b, 72a, 72b, 72c are formed from a supple material, such as a natural or synthetic cloth, having substantially the same characteristics as the material of support straps 14, 16, although the material of guide straps 80, 82 can be elastic to enable stretching thereof.

A distal retention strap pad 84 is attached to the inside of distal shell retention straps 72a, 72b by means such as stitching. Pad 84 covers substantially the entire opening 86 of shell 12 opposite distal cuff 22 to more uniformly distribute the load of distal shell retention straps 72a, 72b across the underlying limb for the comfort of the user. Pad 84 is preferably covered with a soft cloth, such as felt or the like, enclosing a foam cushion.

Figure 4:
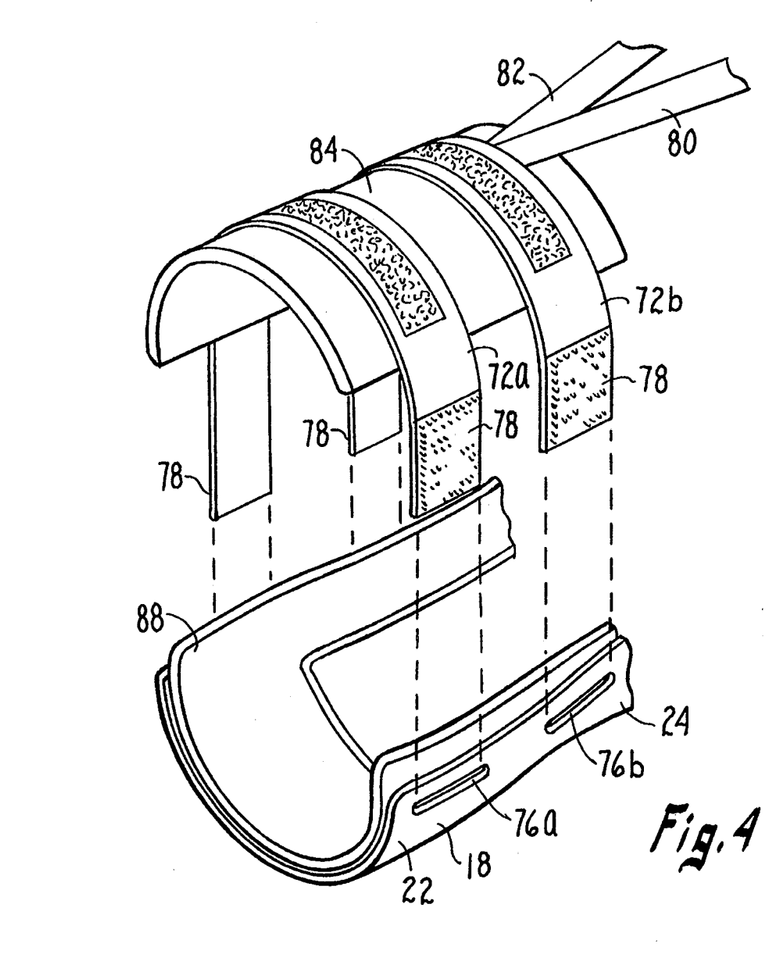
FIG. 4 is an exploded frontal perspective view of the distal portion of the orthopedic brace of FIG. 1.

The preferred relationship between the distal retention strap pad 84, distal shell retention straps 72a, 72b, lateral and medial guide straps 80, 82, and the distal portion 18 of shell 12 is shown in greater clarity with reference to FIG. 4. As recited above, distal shell retention strap 72b serves as a retention member for the attachment of guide straps 80, 82 thereto, thus enabling the connection of guide straps 80, 82 to shell 12 thereacross. In an alternate configuration (not shown), however, it is apparent that the distal retention strap pad 84 can serve as the retention member for the attachment of guide straps 80, 82 thereto, effectuating the connection of guide straps 80, 82 to shell 12.

It is further noted with reference to FIGS. 1–4 that the distal portion 18 and proximal portion 20 of shell 12 are fitted with distal and proximal shell pads 88, 90, respectively. Shell pads 88, 90 are shaped in substantial conformance with the outline of the distal and proximal portions 18, 20. Shell pads 88, 90 enable a close fit of the brace 10 or 62 on the limb of a user and cushion the user from the stiffened inner surface of the shell 12. Pads 88, 90 are constructed from a cloth-covered foam material and are removably attached to the inner surface of the shell 12 by means of a plurality of hook and loop fasteners not shown.

Although braces 10 and 62 have been shown in FIGS. 1–3 and described above as having the distal and proximal cuffs 22, 28 positioned on opposite sides of brace 10 or 62, it is within the scope of the present invention to position the distal and proximal cuffs 22, 28 on the same side of brace 10 or 62, either anteriorly or posteriorly. In these embodiments, the support straps 14, 16 are, nevertheless, connected to the distal and proximal cuffs 22, 28, although connection to one of cuffs 22 or 28 is indirect, while connection to the remaining cuff is direct.

As defined herein, an indirect connection is one wherein the support strap 14 or 16 is interveningly attached to a retention member, such as a retention strap or retention strap pad, which in turn is attached to a cuff 22 or 28. A direct connection is one wherein the support strap 14 or 16 is attached directly to cuff 22 or 28 without attachment to any intervening members. Thus, in these embodiments, one of the engagement points for the support straps 14, 16 is on a retention member and the other engagement point remains on cuff 22 or 28.

Figure 5:
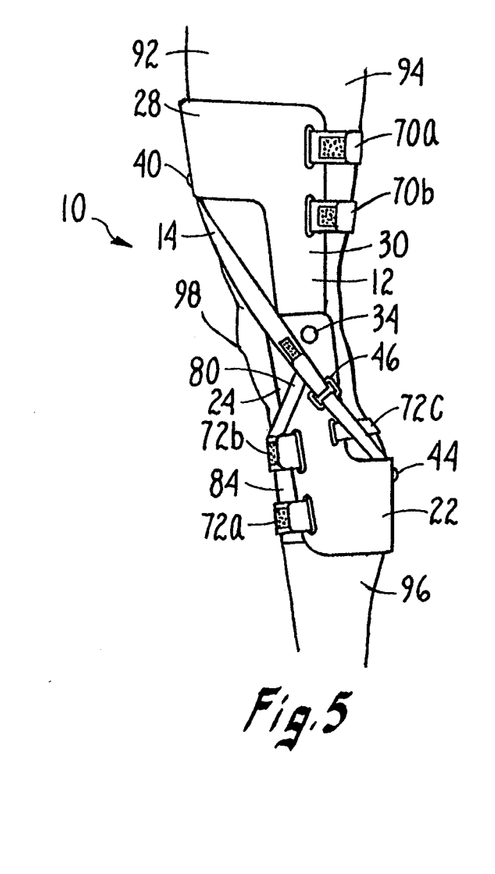
FIG. 5 is a side elevational view of the orthopedic brace of the present invention adapted as a knee brace in place on the leg of a user with the knee joint in an extended position.
Figure 6:
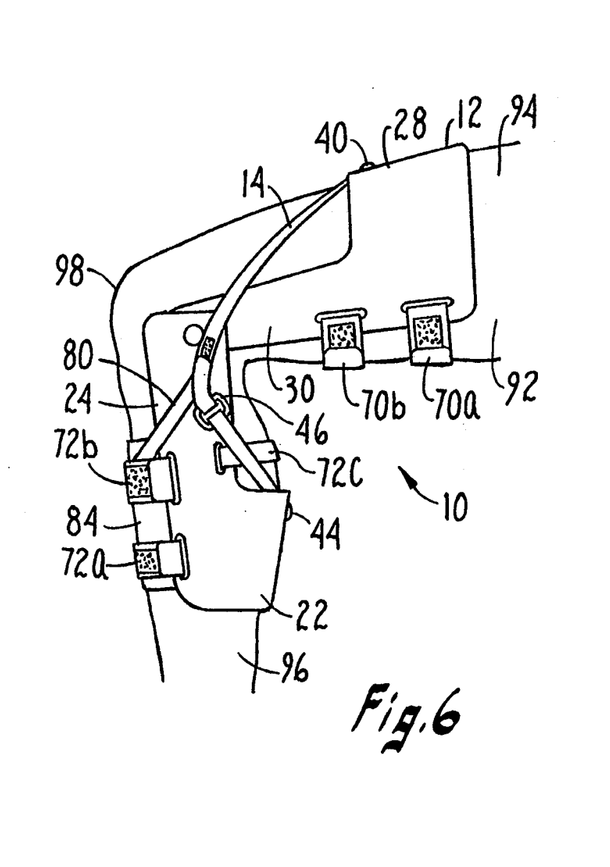
FIG. 6 is a side elevational view of the knee brace of FIG. 5 wherein the knee joint is in a flexed position.
Figure 7:
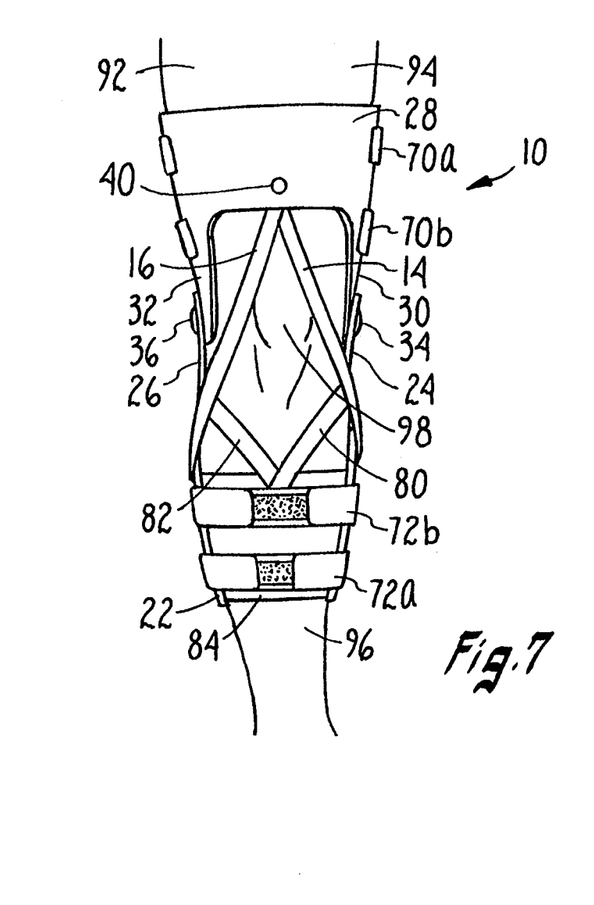
FIG. 7 is a front elevational view of the knee brace of FIG. 5.

Referring to FIGS. 5–7, brace 10 is shown in use mounted on the leg 92 of a user. In the preferred configuration of brace 10, the proximal cuff 28 is positioned on the anterior of the leg 92 against the thigh of the upper leg 94 while the distal cuff 22 is positioned on the posterior of the leg 92 against the calf of the lower leg 96. It is understood by the skilled artisan, however, that these positions can be reversed with the proximal cuff posteriorly positioned and the distal cuff anteriorly positioned. Cuffs 28, 22, being preferably formed from sheet material, are fully conformable to the leg 92 and have a relatively smooth even broad outer surface that is substantially free of protrusions and flush with the outer surface of the leg 92 to minimize interference from the brace 10 during use thereof, and particularly during use in athletic activities, such as soccer.

Lateral and medial proximal arms 30, 32 distally extend from the proximal cuff 28 in correspondence to the longitudinal axis of the upper leg 94. Similarly, the lateral and medial distal arms 24, 26 proximally extend from the distal cuff 22 in correspondence to the longitudinal axis of the lower leg 96. Arms 24, 26, 30, 32 define the opening 68 on the anterior of brace 10 which receives the patella 98. Lateral and medial support straps 14, 16 pass diagonally along opposite sides of the patella 98 and lateral and medial guide straps 80, 82 likewise pass diagonally along opposite sides of the patella 98.

It is noted that when the brace of the present invention is adapted for use with other applicable joints of the body, the opening framed by the arms is generally positioned on the side of the brace opposite the direction of joint flexion to receive the skeletal protrusion of the joint being supported. The support straps and guide straps are generally positioned to extend around the perimeter of the opening, framing the skeletal protrusion therein.

Brace 10, as shown in FIGS. 5–7, is configured to function as a four-point brace in the manner disclosed by U.S. Pat. No. 4,697,583, which is incorporated herein by reference. The four points of brace 10 which supply counteractive support forces to the leg 92 are proximal cuff 28, proximal shell retention strap 70b, distal cuff 22, and distal shell retention strap 72b.

When applied to support of the knee joint, brace 10 is specifically applicable to support of the medial collateral ligament (MCL), to support of the lateral collateral ligament (LCL), or to support of both the MCL and LCL simultaneously. In support of the MCL, the lateral support strap 14 receives outwardly directed loads applied to the medial side of the knee joint and effectively prevents valgus rotation of the knee joint up to the preload limit of the brace 10, thereby reducing the load on the MCL. In this mode, the primary support function of the brace 10 is borne by the lateral support strap 14 while the medial support strap 16 provides a resisting moment to maintain the position of the brace 10 relative to the leg 92 and prevent rotation of proximal cuff 28 axially about the leg 92 relative to distal cuff 22.

In support of the LCL, the medial support strap 16 receives inwardly directed loads applied to the lateral side of the knee joint and effectively prevents varus rotation of the knee joint up to the preload limit of the brace 10, thereby reducing the load on the LCL. In this mode, the primary support function of the brace 10 is borne by the medial support strap 16 while the lateral support strap 14 provides a resisting moment to maintain the position of the brace 10 relative to the leg 92 and prevent rotation of distal cuff 22 axially about the leg 92 relative to proximal cuff 28.

The preload limit of the brace 10 is a function of the length, and correspondingly the tension, of support straps 14, 16, which are adjustable according to the manner described above. In general, it is desirable to set the tension of the support straps 14, 16 to a maximum preload limit defined by the comfort threshold of the user because, if the load on brace 10 exceeds the preload limit of the brace 10, the brace 10 will begin to yield, enabling valgus or varus rotation of the joint.

It is noted that the preload limit of the brace 10 is greater than the preload limit of the support straps 14, 16 alone because when the load on support straps 14, 16 exceeds the preload limit of the straps 14, 16, the load is transferred to shell 12. The combination of support components, specifically shell 12 and support straps 14, 16, effectively resists valgus or varus rotation of the joint due to the relative positions and geometry of the components about the joint, and further, due to the continued action of the support straps 14, 16 to prevent rotation of the distal cuff 22 relative to the proximal cuff 28 axially about the limb.

As is apparent, the efficacy of the brace 10 derives from the ability of the support straps 14, 16 to prevent valgus rotation of the joint, thereby protecting the MCL, when a medial load is applied to the associated limb and/or to prevent varus rotation of the joint, thereby protecting the LCL, when a lateral load is applied to the associated limb. In particular, if a lateral load is applied to the limb, the load is translated to tension on the medial support strap 16 and compression on the lateral arms 24, 30. The lateral load is further translated to tension on the lateral support strap 14 which serves to prevent axial rotation of cuffs 22, 28 due to the tension on medial support strap 16.

Conversely, if a medial load is applied to the limb, the load translates to tension on the lateral support strap 14 and compression on the medial arms 26, 32. The medial load is further translated to tension on the medial support strap 16 which serves to prevent axial rotation of cuffs 22, 28 due to the tension on lateral support strap 14.

From the description set forth above, it is apparent to the skilled artisan that, although the brace of the present invention utilizes compliant support components, the brace, nevertheless, achieves the desired effect of stabilizing the joint by providing control and stability thereto. This effect results from the specific orientation of the compliant support components relative to each other and to the limb on which the brace is mounted, as taught herein, which enables the compliant support components in combination to resist valgus or varus rotation of the joint.

While the forgoing preferred embodiments of the invention have been described and shown, it is understood that alternatives and modifications, such as those suggested and others, may be made thereto and fall within the scope of the invention.

I claim:

1. An orthopedic brace having an anterior side, a posterior side, a medial side and a lateral side, wherein said brace is substantially free of any rigid support components and is mountable on a leg for supporting a knee joint between the upper and lower leg, said brace comprising:
   a) a compliant shell comprising,
      1) an upper leg cuff adapted to be conformingly positioned on the upper leg, and
      2) a lower leg cuff adapted to be conformingly positioned on the lower leg;
   b) means pivotally engaging said shell for rotating said upper leg cuff relative to said lower leg cuff about the knee joint; and
   c) a support strap engaging a first engagement point substantially on the anterior side of said brace that is adapted to be positioned substantially adjacent to the anterior side of the upper leg, and engaging a second engagement point substantially on the posterior side of said brace that is adapted to be positioned substantially adjacent to the posterior side of the lower leg, such that said support strap is adapted to extend from said first engagement point substantially laterally or medially across the knee joint to said second engagement point.

2. The orthopedic brace of claim 1 wherein said first engagement point is on said upper leg cuff and said second engagement point is on said lower leg cuff.

3. The orthopedic brace of claim 1 wherein said support strap is a first support strap adapted to extend from said first engagement point substantially medially across the knee joint to said second engagement point.

4. The orthopedic brace of claim 3 further comprising a second support strap engaging said brace substantially at said first and second engagement points, such that said second support strap is adapted to extend from said first engagement point substantially laterally across the knee joint to said second engagement point.

5. The orthopedic brace of claim 4 wherein said first engagement point fixably engages said first and second support straps.

6. The orthopedic brace of claim 4 wherein said second engagement point fixably engages said first and second support straps.

7. The orthopedic brace of claim 4 wherein said first and second support straps are a unitary strap slidably engaged by said first engagement point.

8. The orthopedic brace of claim 4 wherein said first and second support straps are a unitary strap slidably engaged by said second engagement point.

9. The orthopedic brace of claim 1 wherein said support strap is adapted to extend from said first engagement point substantially laterally across the knee joint to said second engagement point.

10. The orthopedic brace of claim 1 further comprising a guide strap having a first end attached to said support strap and a second end connected to said shell.

11. (amended) The orthopedic brace of claim 1 wherein said shell further comprises,
a lateral upper leg arm and a medial upper leg arm, said upper leg arms connected to said upper leg cuff and adapted to extend distally therefrom generally longitudinal to the thigh, and
a lateral lower leg arm and a medial lower leg arm, said lower leg arms connected to said lower leg cuff and adapted to extend proximally therefrom generally longitudinal to the calf.

12. The orthopedic brace of claim 11 wherein said rotating means comprises a first pin pivotally connecting said lateral upper leg arm to said lateral lower leg arm and a second pin pivotally connecting said medial upper leg arm to said medial lower leg arm.

13. An orthopedic brace substantially free of any rigid support components mountable on a limb for supporting a joint between the proximal and distal portions of the limb, said orthopedic brace comprising:
a) a compliant shell comprising,
1) a proximal cuff adapted to be conformingly positioned on the proximal portion of the limb, and
2) a distal cuff adapted to be conformingly positioned on the distal portion of the limb;
b) means pivotally engaging said shell for rotating said proximal cuff relative to said distal cuff about the joint;
c) a first support strap engaging a first side of said brace at a first engagement point that is adapted to be positioned adjacent to the proximal portion of the limb and engaging a second side of said brace at a second engagement point that is substantially opposite said first side, said second engagement point adapted to be positioned adjacent to the distal portion of the limb, such that said first support strap is adapted to extend from said first side of said brace substantially medially across the joint to said second side of said brace; and
d) a second support strap engaging said brace substantially at said first engagement point, such that said second support strap is adapted to extend from said first side of said brace substantially laterally across the joint toward said second side of said brace.

14. The orthopedic brace of claim 13 wherein said first engagement point is on said proximal cuff and said second engagement point is on said distal cuff.

15. The orthopedic brace of claim 13 wherein said second support strap engages said brace substantially at said second engagement point.

16. An orthopedic brace having an anterior side, a posterior side, a medial side and a lateral side, wherein said brace is substantially free of any rigid support components and is mountable on a leg for supporting a knee joint between the upper and lower leg, said brace comprising:
a) a compliant shell comprising,
1) an upper leg cuff adapted to be conformingly positioned on the anterior side of the upper leg, and
2) a lower leg cuff adapted to be conformingly positioned on the posterior side of the lower leg;
b) means pivotally engaging said shell for rotating said upper leg cuff relative to said lower leg cuff about the knee joint;
c) a first support strap engaging said shell at a first engagement point on said upper leg cuff and substantially on the anterior side of said brace and a second engagement point on said lower leg cuff and substantially on the posterior Side of said brace, such that said support strap is adapted to extend from said first engagement point substantially. laterally across the knee joint to said second engagement point; and
d) a second support strap engaging said shell substantially at said first and second engagement points, such that said second support strap is adapted to extend from said first engagement point substantially medially across the knee joint to said second engagement point.

17. The orthopedic brace of claim 16 further comprising a first guide strap having a first end attached to said first support strap and a second end connected to said shell and a second guide strap having a first end attached to said second support strap and a second end connected to said shell.

18. The orthopedic brace of claim 16 wherein said shell further comprises,
a lateral upper leg arm and a medial upper leg arm, said upper leg arms connected to said upper leg cuff and adapted to extend distally therefrom generally longitudinal to the thigh, and
a lateral lower leg arm and a medial lower leg arm, said lower leg arms connected to said lower leg cuff and adapted to extend proximally therefrom generally longitudinal to the calf.

19. An orthopedic brace substantially free of any rigid support components mountable on a leg for supporting a knee joint between the upper and lower leg, said brace comprising:
a) a compliant shell comprising,
1) an upper leg cuff adapted to be conformingly positioned on the upper leg, and
2) a lower leg cuff adapted to be conformingly positioned on the lower leg;
b) means pivotally engaging said shell for rotating said upper leg cuff relative to said lower leg cuff about the knee joint;
c) a first support strap engaging a first side of said brace at a first engagement point that is adapted to be positioned adjacent to the upper leg, and engaging a second side of said brace at a second engagement point substantially opposite said first side, said second engagement point adapted to be positioned adjacent to the lower leg, such that said first support strap is adapted to extend from said first side of said brace substantially medially across the knee joint to said second side of said brace; and
d) a second support strap engaging said brace substantially at said first engagement point, such that said second support strap is adapted to extend from said first side of said brace substantially laterally across the knee joint toward said second side of said brace.

20. The orthopedic brace of claim 19 wherein said first engagement point fixably engages said first and second support straps.

21. The orthopedic brace of claim 19 wherein said first and second support straps are a unitary strap slidably engaged by said first engagement point.

22. The orthopedic brace of claim 19 wherein said second support strap engages said brace substantially at said second engagement point.

23. The orthopedic brace of claim 22 wherein said second engagement point fixably engages said first and second support straps.

24. The orthopedic brace of claim 22 wherein said first and second support straps are a unitary strap slidably engaged by said second engagement point.

* * * * *